(12) United States Patent
Geitz

(10) Patent No.: US 7,799,088 B2
(45) Date of Patent: *Sep. 21, 2010

(54) INTRAGASTRIC PROSTHESIS FOR THE TREATMENT OF MORBID OBESITY

(75) Inventor: Kurt Geitz, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1077 days.

This patent is subject to a terminal disclaimer.

(21) Appl. No.: 11/503,538

(22) Filed: Aug. 10, 2006

(65) Prior Publication Data

US 2007/0038308 A1 Feb. 15, 2007

Related U.S. Application Data

(63) Continuation of application No. 10/795,491, filed on Mar. 8, 2004, now Pat. No. 7,090,699, which is a continuation of application No. 10/057,469, filed on Jan. 25, 2002, now Pat. No. 6,755,869, which is a continuation of application No. 10/007,819, filed on Nov. 9, 2001, now abandoned.

(51) Int. Cl.
*A61F 2/04* (2006.01)

(52) U.S. Cl. .................. 623/23.65; 600/30; 604/96.01; 623/23.7

(58) Field of Classification Search .................. 600/30, 600/37; 604/93.01, 96.01, 103.06, 103.07, 604/103.1, 104, 107; 606/191, 198; 623/23.64–23.67, 623/23.7, 23.75

See application file for complete search history.

(56) References Cited

U.S. PATENT DOCUMENTS

| 4,648,383 | A  | 3/1987  | Angelchik     |
| 5,306,300 | A  | 4/1994  | Berry         |
| 6,461,631 | B1 | 10/2002 | Dunn et al.   |
| 6,675,809 | B2 | 1/2004  | Stack et al.  |

OTHER PUBLICATIONS

Benjamin, S.B., et al., "Double-Blind Controlled Trial of the Garren-Edwards Gastric Bubble: An Adjunctive Treatment for Exogenous Obesity," *Gastroenterology* 95(3):581-588, Sep. 1988.
Coelho, J.C.U., and A.C.L. Campos, "Surgical Treatment of Morbid Obesity," *Current Opinion in Clinical Nutrition and Metabolic Care* 4(3):201-206, May 2001.
Hubert, H.B., et al., "Obesity as an Independent Risk Factor for Cardiovascular Disease: A 26-Year Follow-Up of Participants in the Framingham Heart Study," *Circulation* 67(5):968-977, May 1983.
Kral, J.G., "Gastric Balloons: A Plea for Sanity in the Midst of Balloonacy," *Gastroenterology* 95(1):213-215, Jul. 1988.
Kral, J.G., "Overview of Surgical Techniques for Treating Obesity," *American Journal of Clinical Nutrition* 55:552S-555S, 1992.

(Continued)

*Primary Examiner*—William H. Matthews
(74) *Attorney, Agent, or Firm*—Fay Kaplun & Marcin, LLP

(57) ABSTRACT

A porous weave of bioabsorbable filaments having an open mesh configuration is formed into an oblate shape having dimensions greater than the esophageal opening and gastric outlet of a stomach. The resulting prosthesis is deployed in the stomach and is of a size to be retained in the proximate portion thereof for exerting pressure on the upper fundus. The prosthesis limits the amount of food that may be held within the stomach, and exerts pressure on the fundus to create a sensation of being full, resulting in weight loss.

14 Claims, 2 Drawing Sheets

OTHER PUBLICATIONS

Macgregor, A.M.C. And C.S.W. Rand, "Gastric Surgery in Morbid Obesity: Outcome in Patients Aged 55 Years and Older," *Archives of Surgery* 128(10):1153-1157, Oct. 1993.

Maclean, L.D., et al., "Results of the Surgical Treatment of Obesity," *The American Journal of Surgery* 165:155-162, Jan. 1993.

Mathus-Vliegen, E.M.H., et al., "Intragastric Balloon in the Treatment of Super-Morbid Obesity: Double-Blind, Sham-Controlled, Crossover Evaluation of 500-Milliliter Balloon," *Gastroenterology* 99(2):362-369, Aug. 1990.

Meshkinpour, H., et al., "Effect of Gastric Bubble as a Weight Reduction Device: A Controlled, Crossover Study," *Gastroenterology* 95(3):589-592, Sep. 1988.

Mun, E.C., et al., "Current Status of Medical and Surgical Therapy for Obesity," *Gastroenterology* 120(3):669-681, Feb. 2001.

Pi-Sunyer, F.X., "Medical Hazards of Obesity," *Annals of Internal Medicine* 119(7) (Part 2):655-660, Oct. 1, 1993.

INTRAGASTRIC PROSTHESIS FOR THE TREATMENT OF MORBID OBESITY

CROSS-REFERENCE TO RELATED APPLICATIONS

This application is a continuation of application Ser. No. 10/795,491, filed Mar. 8, 2004, now U.S. Pat. No. 7,090,699, which is a continuation of application Ser. No. 10/057,469, filed Jan. 25, 2002, now U.S. Pat. No. 6,755,869, which is a continuation of application Ser. No. 10/007,819, filed Nov. 9, 2001, now abandoned, the disclosures of which are hereby expressly incorporated by reference.

FIELD OF INVENTION

The present invention pertains to a resilient, flexible, compressible, bio-compatible prosthesis insertable into the stomach to effect weight loss over a controlled period.

BACKGROUND

The incidence of obesity and its associated health-related problems have reached epidemic proportions in the United States. See, for example, P. C. Mun et al., "Current Status of Medical and Surgical Therapy for Obesity" *Gastroenterology* 120:669-681 (2001). Recent investigations suggest that the causes of obesity involve a complex interplay of genetic, environmental, psycho-behavioral, endocrine, metabolic, cultural, and socio-economic factors. Severe obesity is frequently associated with significant comorbid medical conditions, including coronary artery disease, hypertension, type II diabetes mellitus, gallstones, nonalcoholic steatohepatitis, pulmonary hypertension, and sleep apnea.

Estimates of the incidence of morbid obesity are approximately 2% of the U.S. population and 0.5% worldwide. Current treatments range from diet, exercise, behavioral modification, and pharmacotherapy to various types of surgery, with varying risks and efficacy. In general, nonsurgical modalities, although less invasive, achieve only relatively short-term and limited weight loss in most patients. Surgical treatments include gastroplasty to restrict the capacity of the stomach to hold large amounts of food, such as by stapling or "gastric banding." Other surgical procedures include gastric bypass and gastric "balloons" which, when deflated, may be inserted into the stomach and then are distended by filling with saline solution.

The need exists for cost effective, less invasive interventions for the treatment of morbid obesity.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention provides a novel system for treatment of morbid obesity by use of a bioabsorbable gastric prosthesis placed in the stomach through a minimally invasive procedure. The prosthesis takes up space in the stomach so that the stomach can hold a limited amount of food, and preferably exerts pressure on the upper fundus to create a sensation of being full. The material of the prosthesis can be selected to degrade over a predetermined period and pass out of the patient without additional intervention.

In the preferred embodiment, the prosthesis is a porous weave of bioabsorbable filaments having an open mesh configuration. The prosthesis can be formed from a cylindrical stent, such as by reverting the ends of the cylinder and joining them at the center. The filaments preferably have memory characteristics tending to maintain an oblate shape with sufficient resiliency and softness so as not to unduly interfere with normal flexing of the stomach or cause abrasion of the mucus coat constituting the inner lining of the stomach. The prosthesis may be free floating in the stomach, but is shaped so as to be biased against the upper fundus, or it may be tacked in position adjacent to the fundus by bioabsorbable sutures.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The present invention provides a volume-filling prosthesis insertable into the stomach for treatment of morbid obesity by taking up space in the stomach to reduce its capacity and by exerting pressure to create a sensation of being full, particularly on the upper fundus.

Figure 1:
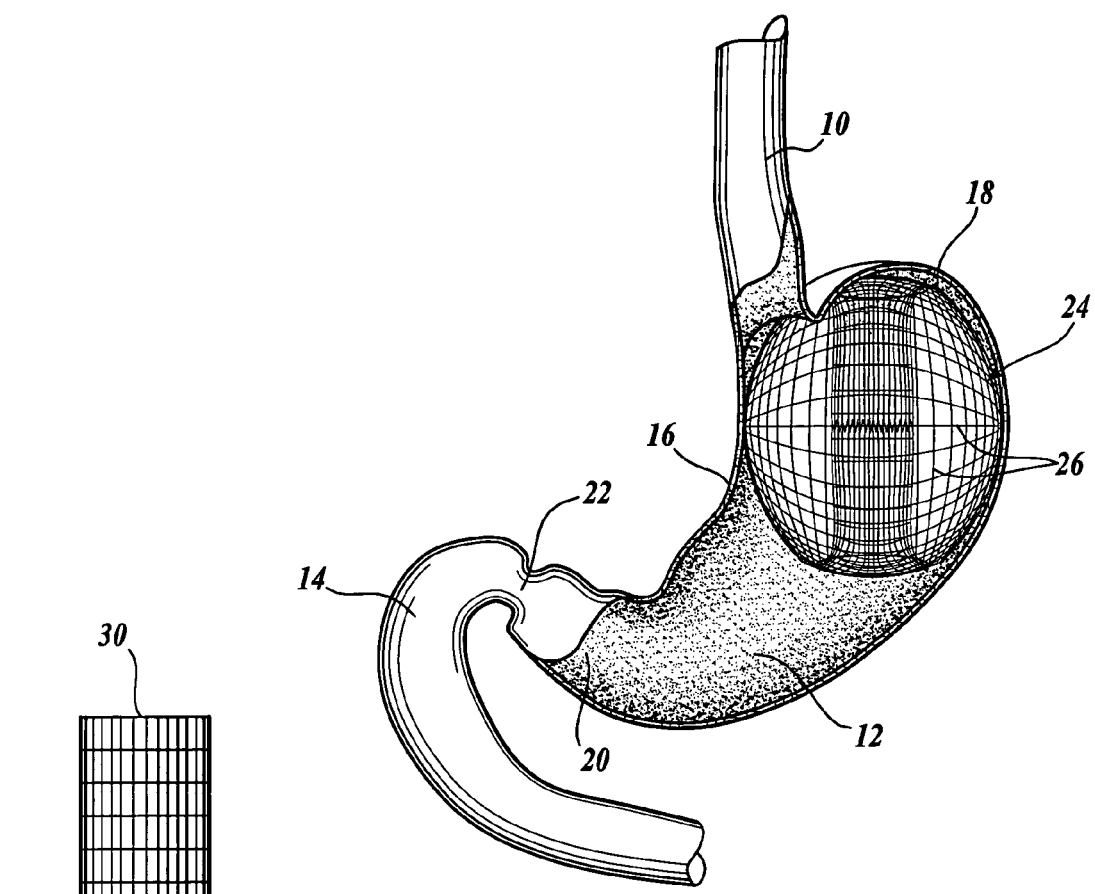
FIG. 1 is a somewhat diagrammatic elevation of a stomach and adjacent parts of the alimentary canal, with the wall adjacent to the viewer partially broken away to reveal an intragastric prosthesis in accordance with the present invention.

FIG. 1 illustrates a central portion of the alimentary canal including the distal segment of the esophagus 10, the stomach 12, and the duodenum 14 (proximate segment of the small intestine). The esophagus 10 opens into the stomach 12 toward the top of the lesser curvature 16 adjacent to the fundus 18. The pyloric part 20 of the stomach leads to the duodenum by way of the gastric outlet or pylorus 22 which forms the distal aperture of the stomach and has an enclosing circular layer of muscle which is normally contracted to close the aperture but which relaxes to provide an open but restricted passage. Although subject to substantial variation in different individuals, representative dimensions for the stomach are approximately 8 cm long (fundus to pylorus) by 5 cm wide (greatest distance between lesser and greater curvatures), with the esophageal opening being approximately 2 cm in diameter and the pylorus having a maximum open diameter of about 2 cm.

In accordance with the present invention, an oblate, volume-filling prosthesis 24 is held within the stomach, sized for reception in the proximate portion adjacent to the opening of the esophagus and fundus. Such prosthesis preferably is a porous body formed of a loose weave of thin polymer filaments 26, having large spaces between filaments for an open area of at least about 80%, preferably more than 90%, so as not to impede the flow of gastric juices or other functioning in the stomach. The filaments 26 have substantial memory characteristics for maintaining the desired oblate shape and size. However, the filaments preferably are sufficiently soft and flexible to avoid abrasion of the mucus coat forming the inner lining of the stomach and to enable normal flexing and shape changes. The size of the prosthesis 24 is substantially greater than the opening of the esophagus, at least about 3 cm in the narrowest dimension, preferably at least about 4 cm. The longer dimension of the oblate prosthesis is greater than 4 cm, preferably at least about 5 cm to prevent the prosthesis from free movement within the stomach. The size and shape of the prosthesis tend to maintain it in the position indicated in FIG. 1, adjacent to the fundus 18 and remote from the pyloric part 20. Thus, while the prosthesis occupies a substantial portion of the volume of the stomach, preferably approximately one-half the volume, the prosthesis does not interfere with normal digestion of food, such as by gastric juices (hydrochloric acid and digestive enzymes) nor with passage of food through the pyloric part 20 and its opening 22 to the duodenum 14.

Figure 2:
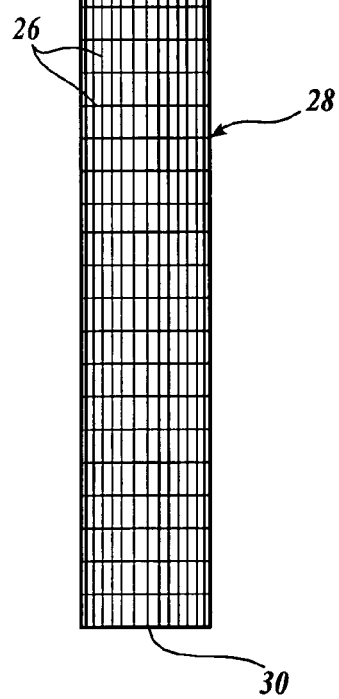
FIG. 2 is a side elevation of a cylindrical stent from which a prosthesis in accordance with the present invention may be formed.

With reference to FIG. 2, the prosthesis can be formed from a substantially cylindrical stent 28 having the desired porous weave and large open area. The filaments 26 and weave pattern are selected to achieve memory characteristics biasing the prosthesis to the cylindrical condition shown. In the preferred embodiment, the opposite ends 30 of the stent are reverted, the end portions are rolled inward, and the ends are secured together such as by suturing. Alternatively, a disk of the same pattern and material can be used in securing the reverted ends together. The resiliency of the filaments tends to bulge the resulting prosthesis 26 outward to the desired oblate shape.

Prior to reversion of the ends, stent 28 in the condition shown in FIG. 2 can be approximately 2-3 cm in diameter and approximately 8-10 cm long, in a representative embodiment. The filaments can have a diameter of about 0.010 inch to about 0.25 inch. The filaments may be coated or impregnated with other treating agents, such as appetite suppressants, or agents to decrease the likelihood of gastric problems, such as ulcers, due to the presence of a foreign object. However, such problems are unlikely due to the biocompatible nature and the resilient flexibility of the prosthesis.

It is preferred that the filaments 26 be formed of a bioabsorbable polymer such as a polyglycolic acid polymer or polylactic acid polymer. Similar materials are used for some bioabsorbable sutures having "forgiving" memory characteristics and sufficient "softness" that tissue abrasion is inhibited. The absorption characteristics of the filaments 26 can be selected to achieve disintegration of the prosthesis 26 within the range of three months to two years, depending on the severity of obesity. In the preferred embodiment, the prosthesis will absorb and pass naturally from the stomach approximately 6 months after deployment.

Nonbioabsorbable materials may be used, such as Nitinol, which exhibit the desired springiness but which would require that the prosthesis be retrieved. An advantage of the preferred, bioabsorbable embodiment of the invention is that delivery can be through the esophagus, with no additional intervention being required.

Figure 3:
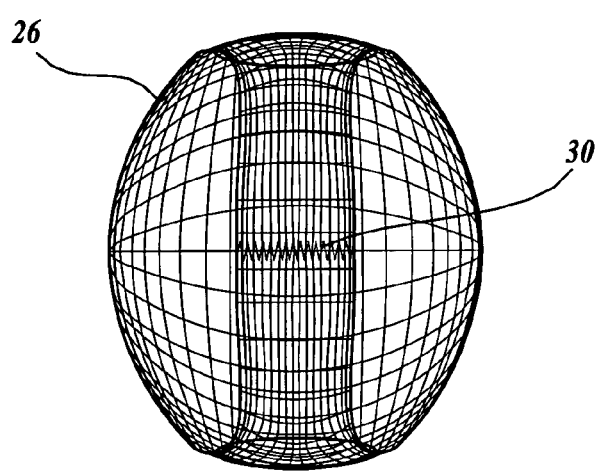
FIG. 3 is a side elevation of a prosthesis in accordance with the present invention, formed from the stent of FIG. 2.
Figure 4:
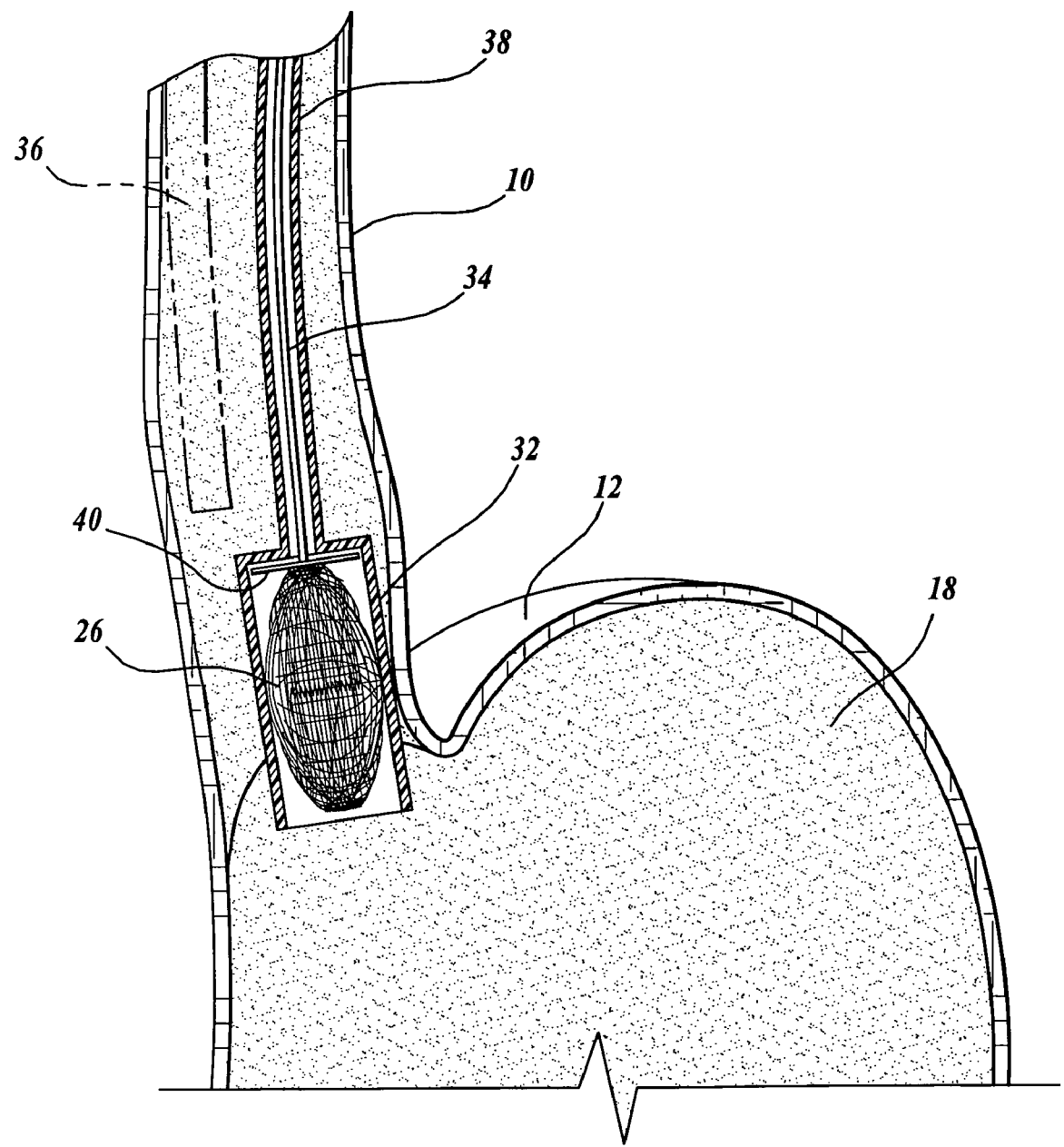
FIG. 4 is a diagrammatic elevation corresponding to FIG. 1, illustrating insertion of a prosthesis in accordance with the present invention through the esophagus and into the stomach.

With reference to FIG. 4, preferably from the condition shown in FIG. 3, the prosthesis 26 can be compressed to a generally cylindrical shape having a diameter of no more than about 2 cm such that the compressed prosthesis can be carried in a short (approximately 5 cm to 6 cm long) loading tube 32.

The loading tube can be advanced along the esophagus by a central tube 34 of smaller diameter, under the visualization allowed by a conventional endoscope 36. The tube 34 can enclose a core wire 38 to actuate a pusher mechanism 40 for ejecting the prosthesis 26 when the opening of the esophagus into the stomach has been reached. The endoscope and deployment mechanism can then be retracted.

While the preferred embodiment of the invention has been illustrated and described, it will be appreciated that various changes can be made therein without departing from the spirit and scope of the invention. For example, while it is preferred that the prosthesis be sized for self-retention in the desired position in the stomach, it also may be secured in position by a few sutures applied endoscopically, preferably in or adjacent to the fundus area of the stomach.

The invention claimed is:

1. An intra-gastric prosthesis comprising an empty porous oblate body formed of a weave of flexible, resilient filaments and sized for reception in a stomach, the size of the oblate body, when deployed in a stomach, being greater than the esophageal opening and the gastric outlet for retention in the stomach, the body being formed of a stent of the filaments with opposite ends of the stent being reverted and secured together, wherein, as a result of the opposite ends being reverted and secured together, the filaments move into a configuration corresponding to the oblate body.

2. The prosthesis defined in claim 1, in which the filaments are bioabsorbable, so that the prosthesis will pass from a stomach without surgical intervention after an approximately predetermined period.

3. The prosthesis defined in claim 2, in which the approximately predetermined period is 3 months to 2 years.

4. The prosthesis defined in claim 3, in which the approximately predetermined period is about six months.

5. The prosthesis defined in claim 1, in which the filaments form a body having an open area of at least 80%.

6. The prosthesis defined in claim 5, in which the filaments form a body having an open area of at least 90%.

7. The prosthesis defined in claim 1, in which the oblate body has a minimum diameter of at least 3 cm.

8. The prosthesis defined in claim 7, in which the oblate body has a minimum diameter of at least 4 cm.

9. The prosthesis defined in claim 1, in which the oblate body has a long dimension greater than 4 cm.

10. The prosthesis defined in claim 9, in which the oblate body has a long dimension at least about 5 cm.

11. The prosthesis defined in claim 1, in which the body is sized for reception in the proximate portion of the stomach adjacent to the fundus for applying pressure to the fundus.

12. The prosthesis defined in claim 1, in which the filaments are coated or impregnated with a medical treating agent.

13. The prosthesis defined in claim 1, in which the body is compressible to a generally cylindrical shape having a diameter of no more than about 2 cm.

14. The prosthesis defined in claim 13, and mechanism for deploying the body in a stomach, such mechanism including a loading member for receiving the body in compressed condition, an advancing member for moving the loading member along the esophagus, and a deployment mechanism for ejecting the body into the stomach whereby the body expands due to memory characteristics of the filaments.

* * * * *